US012014822B2

(12) United States Patent
Taniguchi

(10) Patent No.: US 12,014,822 B2
(45) Date of Patent: Jun. 18, 2024

(54) MACHINE LEARNING DEVICE, TRAINED MODEL, DATA STRUCTURE, PERIODONTAL DISEASE DETECTION METHOD, PERIODONTAL DISEASE DETECTION SYSTEM, AND PERIODONTAL DISEASE DETECTION KIT

(71) Applicant: Mitsui Chemicals, Inc., Tokyo (JP)

(72) Inventor: Makoto Taniguchi, Takamatsu (JP)

(73) Assignee: Mitsui Chemicals, Inc., Tokyo (JP)

( * ) Notice: Subject to any disclaimer, the term of this patent is extended or adjusted under 35 U.S.C. 154(b) by 1329 days.

(21) Appl. No.: 16/488,661

(22) PCT Filed: Feb. 28, 2018

(86) PCT No.: PCT/JP2018/007622
§ 371 (c)(1),
(2) Date: Aug. 26, 2019

(87) PCT Pub. No.: WO2018/159712
PCT Pub. Date: Sep. 7, 2018

(65) Prior Publication Data
US 2020/0234831 A1  Jul. 23, 2020

(30) Foreign Application Priority Data

Mar. 1, 2017  (JP) ................. 2017-038122
Mar. 1, 2017  (JP) ................. 2017-038123

(51) Int. Cl.
*A61C 19/04* (2006.01)
*A61B 5/00* (2006.01)
(Continued)

(52) U.S. Cl.
CPC .......... *G16H 50/20* (2018.01); *A61B 5/4842* (2013.01); *A61C 19/04* (2013.01); *G06F 18/214* (2023.01);
(Continued)

(58) Field of Classification Search
CPC ... A61B 5/0088; A61B 5/4842; A61B 5/7264; C12M 1/00; C12N 15/09; C12Q 1/02;
(Continued)

(56) References Cited

U.S. PATENT DOCUMENTS

2017/0175172 A1* 6/2017 Apte ................. G16B 50/20

FOREIGN PATENT DOCUMENTS

JP  H08249300 A  9/1996
JP  2016-192950 A  11/2016
WO  2014/179959 A1  11/2014

OTHER PUBLICATIONS

16S Metagenomic Sequencing Library Preparation, "Preparing 16S Ribosomal RNA Gene Amplicons for the Illumina MiSeq System", (https://support.illumina.com/content/dam/illumina-support/documents/documentation/chemistry_documentation/16s/16s-metagenomic-library-prep-guide-15044223-b.pdf), pp. 1-28.
(Continued)

*Primary Examiner* — Scott Luan
(74) *Attorney, Agent, or Firm* — BUCHANAN, INGERSOLL & ROONEY PC

(57) ABSTRACT

A machine learning device that includes a training section configured perform training based on plural training data each configured from oral cavity information detected from a specimen and at least one determination value selected from the group consisting of a probability of periodontal disease contraction of a provider of the specimen or a state of periodontal disease, so as to train the function to decide the determination value. The training section includes a reward calculation section, a function updating section, and a convergence determination section. The reward calculation section calculates a reward for a defined result of the probability of periodontal disease contraction or the state of periodontal disease based on the training data. The function updating section updates the function so as to increase the
(Continued)

reward calculated by the reward calculation section. The convergence determination section causes repeated calculations and updates until a predetermined convergence condition is satisfied.

13 Claims, 2 Drawing Sheets

Specification includes a Sequence Listing.

(51) Int. Cl.
- *G06F 18/21* (2023.01)
- *G06F 18/214* (2023.01)
- *G06K 9/62* (2022.01)
- *G06N 3/04* (2023.01)
- *G06N 3/044* (2023.01)
- *G06N 3/063* (2023.01)
- *G06N 20/00* (2019.01)
- *G16H 50/20* (2018.01)
- *G16H 50/70* (2018.01)

(52) U.S. Cl.
CPC ........... *G06F 18/217* (2023.01); *G06N 3/044* (2023.01); *G06N 3/063* (2013.01); *G06N 20/00* (2019.01); *G16H 50/70* (2018.01)

(58) Field of Classification Search
CPC ...... C12Q 1/6893; G16H 10/40; G16H 50/20; G16H 50/70
See application file for complete search history.

(56) References Cited

OTHER PUBLICATIONS

Czibula, et al., "Temporal ordering of cancer microarray data through a reinforcement learning based approach", PLoS One, Apr. 2013, vol. 8(4), pp. 1-12, e60883, ISSN 1932-6203.

Gomes, et al., "Microbiomes of Endodontic-Periodontal Lesions before and after Chemomechanical Preparation", Journal of Endodontics, vol. 41, Issue 12, Dec. 2015, pp. 1975-1984.

International Search Report (PCT/ISA/210) translation and Written Opinion (PCT/ISA/237) mailed on May 29, 2018, by the Japanese Patent Office as the International Searching Authority for International Application No. PCT/JP2018/007622.

Kebschull M. et al., "Exploring Genome-Wide Expression Profiles Using Machine Learning Techniques", Methods Mol. Biol., Dec. 2017, 1537, pp. 347-364, ISSN 1064-3745.

Kebschull, et al., "Molecular differences between chronic and aggressive periodontitis", J. Dent. Res., 2013, vol. 92(12), pp. 1081-1088, ISSN 0022-0345.

Kusy, et al., "Probabilistic neural network training procedure based on Q(0)-learning algorithm in medical data classification", Appl. Intell., 2014, vol. 41(3), pp. 837-854, ISSN 0924-669X.

Szafranski, et al., "High-resolution taxonomic profiling of the subgingival microbiome for biomarker discovery and periodontitis diagnosis", Appl. Environ. Microbiol., Feb. 2015, vol. 81(3), pp. 1047-1058, ISSN 0099-2240.

Notice of Reasons for Rejection issued on Mar. 15, 2022, by the Japanese Patent Office in corresponding Japanese Patent Application No. 2020-176791, and an English Translation of the Notice. (7 pages).

Kistler, J. et al., "Bacterial Community Development in Experimental Gingivitis", Plos One, Aug. 2013, vol. 8, Issue 8, e71227, pp. 1-13.

Abusleme, L. et al., "The subgingival microbiome in health and periodontitis and its relationship with community biomass and inflammation", ISME Journal. 2013, vol. 7, pp. 1016-1025.

Satoshi Tada, First edition of textbooks of artificial intelligence, 1st edition, Mikio Sasaki of Shoeisha Co., Ltd., 2016, p. 218 (3 pages).

Notice of Reasons for Rejection issued on Sep. 1, 2020, by the Japanese Patent Office in corresponding Japanese Patent Application No. 2019-503084, and an English translation of the Notice. (7 pages).

Yost, S. et al. "Functional signatures of oral dysbiosis during periodontitis progression revealed by microbial metatranscriptome analysis", Genome Medicine, 2015, vol. 7, pp. 1-19 and additional file. (25 pages).

Oliveira, R.R.D.S. et al. "Levels of Candidate Periodontal Pathogens in Subgingival Biofilm", Journal of Dental Research, 2016, vol. 95, No. 6, pp. 711-718.

\* cited by examiner

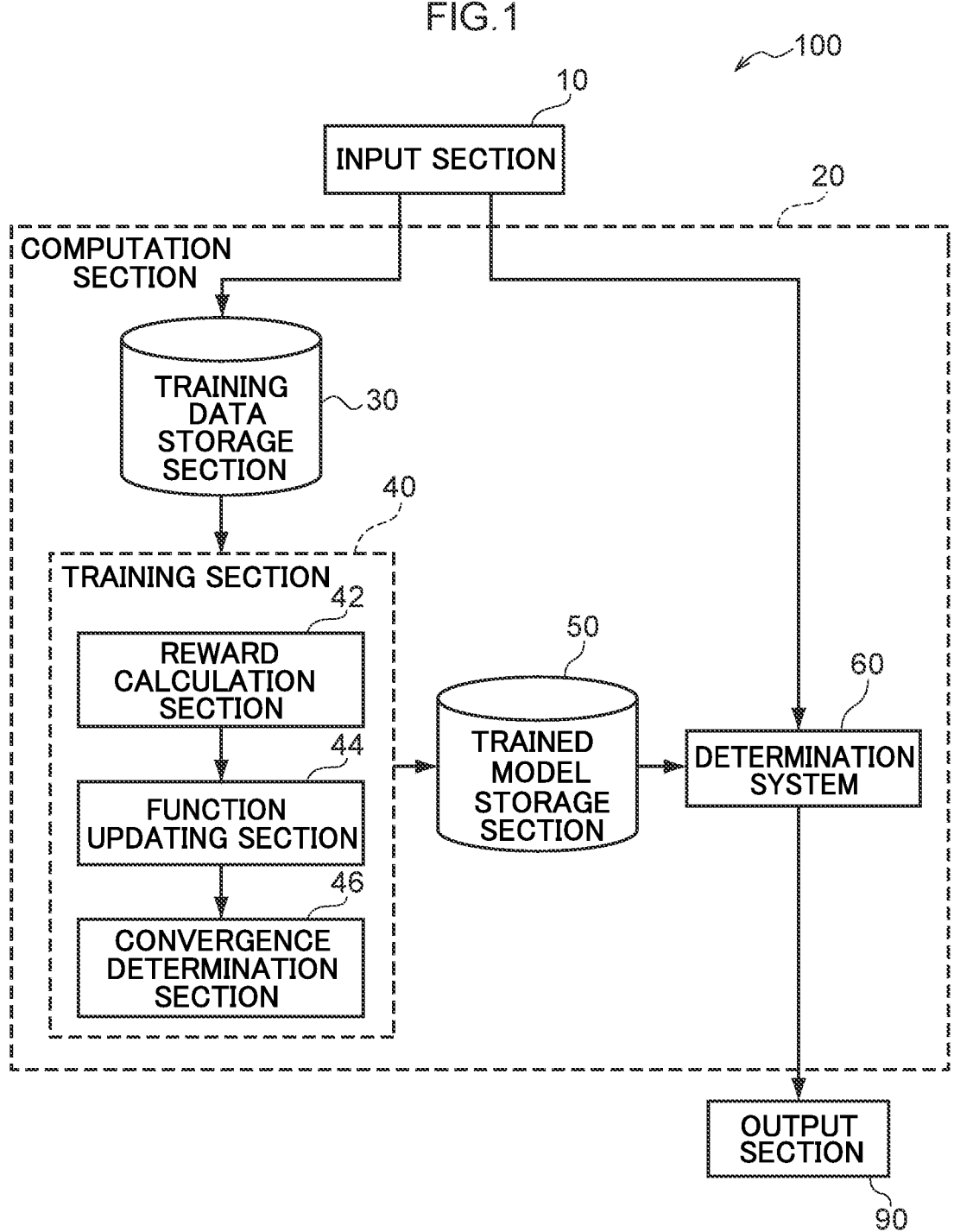

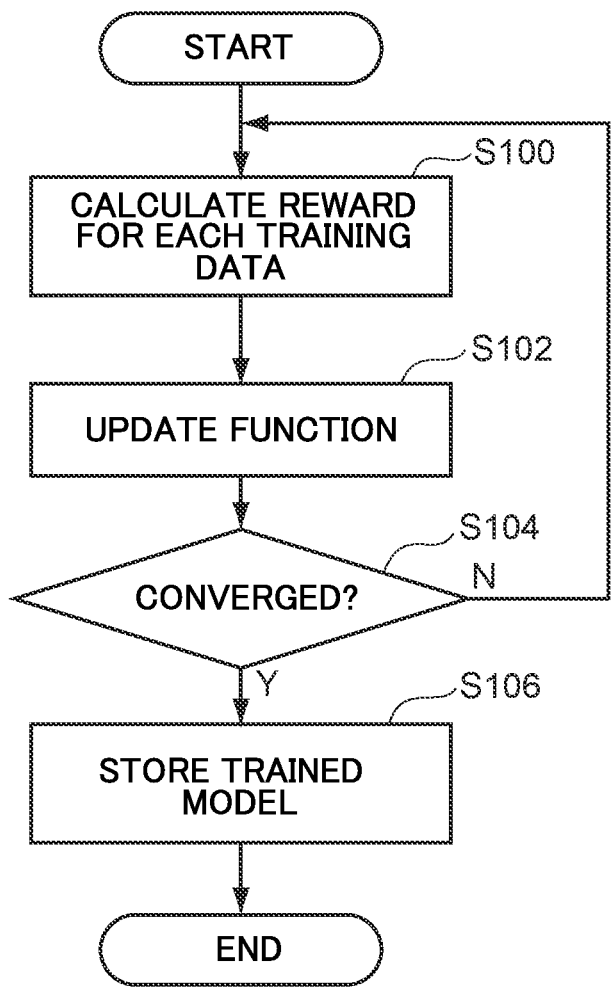

MACHINE LEARNING DEVICE, TRAINED MODEL, DATA STRUCTURE, PERIODONTAL DISEASE DETECTION METHOD, PERIODONTAL DISEASE DETECTION SYSTEM, AND PERIODONTAL DISEASE DETECTION KIT

TECHNICAL FIELD

The present invention relates to a machine learning device, a trained model, a data structure, a periodontal disease detection method, a periodontal disease diagnosis method, a periodontal disease detection system, and a periodontal disease detection kit.

BACKGROUND ART

Various methods for using the state of specific bacteria in the oral cavity to determine whether or not periodontal disease has been contracted are being investigated as methods for detecting periodontal disease. There is, for example, a description in Non-Patent Document 1 regarding a relationship between Fretibacterium and periodontal disease.

RELATED DOCUMENTS

Patent Documents

Non-Patent Document 1: Journal of Endodontics, Volume 41, Issue 12, December 2015 pp. 1975-1984.

SUMMARY OF INVENTION

Technical Problem

Although there are a number of reports regarding a relationship between the state of specific bacteria in the oral cavity and periodontal disease, such as that in Non-Patent Document 1, there is still room for investigation into what kind of information about the oral cavity it is appropriate to form the basis of determination of whether or not periodontal disease has been contracted.

Moreover, the discovery of numerous methods to determine whether or not periodontal disease has been contracted based on oral cavity information would conceivably be beneficial from the perspective of improving detection techniques for periodontal disease, enriching the choices etc. for patients being examined.

In consideration of the above circumstances, an object of the present invention is to provide a novel machine learning device, trained model, and data structure for use in the detection of periodontal disease. An object of the present invention is also to provide a novel periodontal disease detection method, periodontal disease diagnostic method, periodontal disease detection system, and periodontal disease detection kit.

Solution to Problem

Specific ways to achieve the above objects include the following aspects.

<1> A machine learning device for training a function to determine a probability of periodontal disease contraction or a state of periodontal disease.

The machine learning device includes a training section configured perform training based on plural training data each configured from oral cavity information detected from a specimen and at least one determination value selected from the group consisting of a probability of periodontal disease contraction of a provider of the specimen or a state of periodontal disease, so as to train the function to decide the determination value.

The training section includes a reward calculation section configured to use the function to calculate a reward for a defined result of the probability of periodontal disease contraction or the state of periodontal disease based on the training data, a function updating section configured to update the function so as to increase the reward calculated by the reward calculation section, and a convergence determination section configured to cause calculations by the reward calculation section and updating by the function updating section to be repeated until a predetermined convergence condition is satisfied.

<2> The machine learning device of <1>, wherein the oral cavity information includes oral cavity microbiome information.

<3> The machine learning device of <1> or <2>, further including a determination section configured to use the function as trained by the training section to decide the determination value from the oral cavity information that has been input.

<4> A trained model to cause a computer to function based on data related to oral cavity information detected from a specimen by functioning so as to output a value expressing a probability of periodontal disease contraction of a provider of the specimen or a state of periodontal disease.

The trained model includes a first neural network and a second neural network combined with the first neural network such that the output from the first neural network is input to the second neural network.

The first neural network is a neural network having a number of neurons in at least one middle layer that is less than a number of neurons in an input layer and there is also the same number of neurons in the input layer and an output layer of the first neural network, with weighting coefficients of the first neural network being trained such that input values to each of the input layers and output values from each of the output layers corresponding to the respective input layers are equal to each other.

A portion of the model from the input layer to the middle layer of the first neural network is employed as a feature extraction neural network.

Weighting coefficients in the second neural network are trained without changing the weighting coefficients in the first neural network.

The trained model causes the computer to function such that when an appearance frequency of specific information obtained from data related to the oral cavity information detected from the specimen has been input to the input layer of the first neural network, computation is performed based on the trained weighting coefficients in the first and second neural networks so as to output from the output layer of the second neural network a value expressing a probability of periodontal disease contraction or a state of periodontal disease.

<5> The trained model of <4>, wherein the oral cavity information includes oral cavity microbiome information.

<6> A data structure including oral cavity information detected from a specimen and information identifying a provider of the specimen.

The data structure is used for processing based on the oral cavity information in which a trained model, which has been pre-trained so as to output a value expressing a probability of periodontal disease contraction of the specimen provider or a state of periodontal disease, is employed to compute a probability related to periodontal disease contraction or a state of periodontal disease.

<7> The data structure of <6>, wherein the oral cavity information includes oral cavity microbiome information.

<8> A periodontal disease detection method including a detection process to detect in a specimen at least two bacterial strains selected from the group consisting of *Anaeroglobus*, *Cryptobacterium*, *Desulfobulbus*, *Desulfomicrobium*, *Desulfovibrio*, Erysipelotrichaceae, Fretibacterium, *Johnsonella*, *Mitsuokella*, Mollicutes, *Parascardovia*, *Pseudoramibacter*, *Pyramidobacter*, *Scardovia*, *Shuttleworthia*, and *Mycoplasma*.

<9> The periodontal disease detection method of <8>, wherein the at least two bacterial strains included in the group are at least two bacterial strains selected from the group consisting of *Anaeroglobus*, Fretibacterium, and *Mycoplasma*.

<10> The periodontal disease detection method of <8> or <9>, further including an evaluation process after the detection process to evaluate a possibility that a provider of the specimen has contracted periodontal disease based on a result obtained in the detection process.

<11> The periodontal disease detection method of <10>, wherein the evaluation process includes an analysis process to calculate a sum total of a number of sequence reads obtained in the detection process and a sum total of a number of sequence reads of the at least two bacterial strains included in the group, and evaluation is performed in the evaluation process based on an analysis result obtained by the analysis process.

<12> The periodontal disease detection method of <10> or <11>, wherein the evaluation process evaluates the possibility that the specimen provider has contracted periodontal disease as high in cases in which the sum total of the number of sequence reads of the at least two bacterial strains included in the group is 0.02% or more with respect to the sum total of the number of sequence reads obtained in the detection process of 100%.

<13> The periodontal disease detection method of any one of <8> to <12>, wherein the detection is performed by metagenomic analysis.

<14> The periodontal disease detection method of any one of <8> to <13>, wherein the specimen is saliva.

<15> A periodontal disease detection system including a detection section to detect in a specimen at least two bacterial strains selected from the group consisting of *Anaeroglobus*, *Cryptobacterium*, *Desulfobulbus*, *Desulfomicrobium*, *Desulfovibrio*, Erysipelotrichaceae, Fretibacterium, *Johnsonella*, *Mitsuokella*, Mollicutes, *Parascardovia*, *Pseudoramibacter*, *Pyramidobacter*, *Scardovia*, *Shuttleworthia*, and *Mycoplasma*.

<16> A periodontal disease detection kit including a detection device to detect in a specimen at least two bacterial strains selected from the group consisting of *Anaeroglobus*, *Cryptobacterium*, *Desulfobulbus*, *Desulfomicrobium*, *Desulfovibrio*, Erysipelotrichaceae, Fretibacterium, *Johnsonella*, *Mitsuokella*, Mollicutes, *Parascardovia*, *Pseudoramibacter*, *Pyramidobacter*, *Scardovia*, *Shuttleworthia*, and *Mycoplasma*.

<17> A periodontal disease detection method including a detection process to detect in a specimen at least one bacterial strain selected from the group consisting of GN02, *Ottowia*, *Sneathia*, and *Lautropia*.

<18> The periodontal disease detection method of <17>, wherein the at least one bacterial strain included in the group includes *Lautropia*.

<19> The periodontal disease detection method of <17> or <18>, wherein the at least one bacterial strain included in the group is a combination of *Lautropia* combined with at least one bacterial strain selected from the group consisting of GN02, *Ottowia*, and *Sneathia*.

<20> The periodontal disease detection method of any one of <17 to <19>, further including an evaluation process after the detection process to evaluate a possibility that a provider of the specimen has contracted periodontal disease based on a result obtained in the detection process.

<21> The periodontal disease detection method of <20>, wherein the evaluation process includes an analysis process to calculate a sum total of a number of sequence reads obtained in the detection process and a sum total of a number of sequence reads of the at least two bacterial strains included in the group, and evaluation is performed in the evaluation process based on an analysis result obtained by the analysis process.

<22> The periodontal disease detection method of <20> or <21>, wherein the evaluation process evaluates the possibility that the specimen provider has contracted periodontal disease as high in cases in which the sum total of the number of sequence reads of the at least one bacterial strain included in the group is 0.01% or less with respect to the sum total of the number of sequence reads obtained in the detection process of 100%.

<23> The periodontal disease detection method of any one of <17 to <22>, wherein the detection is performed by metagenomic analysis.

<24> The periodontal disease detection method of any one of <17 to <23>, wherein the specimen is saliva.

<25> A periodontal disease detection system including a detection section to detect in a specimen at least one bacterial strain selected from the group consisting of GN02, *Ottowia*, *Sneathia*, and *Lautropia*.

<26> A periodontal disease detection kit including a detection device to detect in a specimen at least one bacterial strain selected from the group consisting of GN02, *Ottowia*, *Sneathia*, and *Lautropia*.

Advantageous Effects

The present invention provides a novel machine learning device, trained model, and data structure for use in the detection of periodontal disease. The present invention also provides a novel periodontal disease detection method, periodontal disease diagnostic method, periodontal disease detection system, and periodontal disease detection kit.

BRIEF DESCRIPTION OF DRAWINGS

FIG. 1 is a schematic diagram illustrating an example of a configuration of a machine learning device 100.

FIG. 2 is a schematic diagram illustrating an example of a machine learning processing routine of the machine learning device 100.

DESCRIPTION OF EMBODIMENTS

Detailed explanation follows regarding embodiments for implementing the present invention. However, the present invention is not limited by the following exemplary embodiments.

In the present disclosure, the word "process" includes, in addition to a process independent from another process, a process capable of achieving the purpose of a process even in cases in which the process is not able to be clearly distinguished from another process.

Machine Learning Device

The machine learning device of the present exemplary embodiment is a machine learning device to train a function for determining a probability of periodontal disease contraction or a state of periodontal disease.

The machine learning device includes a training section configured perform training based plural training data each configured from oral cavity information detected from a specimen and at least one determination value selected from the group consisting of a probability of periodontal disease contraction of a provider of the specimen or a state of periodontal disease, so as to train the function to decide the determination value.

The training section includes a reward calculation section configured to use the function to calculate a reward for a defined result of the probability of periodontal disease contraction or the state of periodontal disease based on the training data, a function updating section configured to update the function so as to increase the reward calculated by the reward calculation section, and a convergence determination section configured to cause calculations by the reward calculation section and updating by the function updating section to be repeated until a predetermined convergence condition is satisfied.

The above machine learning device may be used to determine whether or not a specimen provider has contracted periodontal disease, determine whether or not periodontal disease is being cured, determine whether or not periodontal disease is curable, determine whether or not periodontal disease is progressing, and the like.

In an exemplary embodiment saliva is used as the specimen, however, there is no limitation thereto. For example, the specimen may be gingival crevicular fluid, dental plaque, a biofilm, a tongue coating, and the like. In particular using saliva as the specimen enables oral cavity information to be obtained for the specimen provider by a simple technique without damaging the gums or the like when taking the specimen.

Although an example is given in which the oral cavity microbiome (including base sequence reads of bacteria) is employed as the oral cavity information to be detected in the specimen, there is no limitation thereto. In an exemplary embodiment, the oral cavity information is information regarding the bacterial strains listed in a periodontal disease detection method (1) or (2), described below, may be employed. Specific examples of information that may be utilized therefor include: a sum of branch lengths between bacteria in a phylogenetic tree (UniFrac distance); a number of reads (sequence and read quantity) obtained by next-generation sequencing; a type and quantity of inter-bacterial signaling (quorum sensing, autoinducer); a type and quantity of mutually syntrophic relationships between bacteria; bacterial growth conditions (oxygen demand, nutrient demand, etc.); a type and quantity of antigens affecting immune function; a type and quantity of protease for breaking down biological structures; a type and quantity of polynucleotides related to gene expression or gene control; a type and quantity of endotoxins and lipopolysaccharides configuring the outer membrane of cell walls of bacteria; a feature value expressing bacterial function; and the like. Each such information may be applied with a prescribed weighting and combined, or feature values may be obtained after characteristic extraction in main component analysis, and these then combined.

Examples of at least one determination value selected from the group consisting of a probability of periodontal disease contraction and a state of periodontal disease include a determination value based on the presence or absence of, or the proportion of, specific bacterial strains in the oral cavity microbiome, however there is no limitation thereto. In an exemplary embodiment the determination value may be based on the presence or absence of, or the proportion of, a bacterial strain listed in the periodontal disease detection method (1) or (2), described below.

The training data referred to above may include other information, as required. Examples of such other information include, for the specimen provider: an age, gender, smoking habits, and eating habits; a status of oral care implementation; a dental treatment history; a presence or absence of a chronic or pre-existing dental disorder and dental caries; a dental alignment; a volume of saliva; a state of oral cavity hygiene; a habit (such as bruxism, mouth-breathing, and the like); a state of stress; and the like.

The machine learning device of the present exemplary embodiment may further include a determination section to decide on the determination value described above from the input oral cavity information using the function as trained by the training section.

FIG. 1 is a schematic diagram illustrating an example of a configuration of a machine learning device 100. The machine learning device 100 configured as illustrated in FIG. 1 may be configured by a computer include a CPU, RAM, and ROM stored with a program to execute a machine learning processing routine, described later, and with various data. The machine learning device 100 includes an input section 10, a computation section 20, and an output section 90, as illustrated functionally in FIG. 1.

The input section 10 receives plural training data each configured from oral cavity information detected a specimen and at least one determination value selected from the group consisting of a probability of periodontal disease contraction of the specimen provider and a state of periodontal disease. The input section 10 also receives as a determination subject oral cavity information detected from the specimen.

The computation section 20 includes a training data storage section 30, a training section 40, a trained model storage section 50, and a determination section 60.

The plural training data received by the input section 10 is stored in the training data storage section 30.

The training section 40 trains a function for deciding on the determination value based on the plural training data. This function is a trained model, described later.

Specifically, the training section 40 includes a reward calculation section 42, a function updating section 44, and a convergence determination section 46.

The reward calculation section 42 uses the function to calculate, for each of the plural training data, a reward for a defined result of the probability of periodontal disease contraction or the state of periodontal disease based on the training data.

The function updating section 44 updates the function so as to increase the reward based on the rewards calculated by the reward calculation section 42 for each of the plural training data.

The convergence determination section 46 causes the calculations by the reward calculation section 42 and the updating by the function updating section 44 to be repeated until a predetermined convergence condition is satisfied.

The trained model storage section 50 stores the function as trained by the training section 40.

The determination section 60 takes the oral cavity information detected from the specimen input as the determination subject and uses the function as trained by the training section 40 to decide on at least one determination value selected from the group consisting of a probability of periodontal disease contraction and a state of periodontal disease for the specimen provider.

There is no particular limit to each of the configuration elements of the machine learning device of the present exemplary embodiment, and each of the configuration elements of any known machine learning device may be employed therefor.

Trained Model

The trained model of the present exemplary embodiment is a trained model to cause a computer to function based on data related to oral cavity information detected from a specimen by functioning so as to output a value expressing a probability of periodontal disease contraction of a provider of the specimen or a state of periodontal disease.

The trained model includes a first neural network and a second neural network combined with the first neural network such that the output from the first neural network is input to the second neural network.

The first neural network is a neural network having a number of neurons in at least one middle layer that is less than a number of neurons in an input layer and there is also the same number of neurons in the input layer and an output layer of the first neural network, with weighting coefficients of the first neural network being trained such that input values to each of the input layers and output values from each of the output layers corresponding to the respective input layers are equal to each other.

A portion of the model from the input layer to the middle layer of the first neural network is employed as a feature extraction neural network.

Weighting coefficients in the second neural network are trained without changing the weighting coefficients in the first neural network.

The trained model causes the computer to function such that when an appearance frequency of specific information obtained from data related to the oral cavity information detected from the specimen has been input to the input layer of the first neural network, computation is performed based on the trained weighting coefficients in the first and second neural networks so as to output from the output layer of the second neural network a value expressing a probability of periodontal disease contraction of the specimen provider or a state of periodontal disease.

The trained model configured as described above may be used to determine whether or not the specimen provider has contracted periodontal disease, determine whether or not periodontal disease is being cured, determine whether or not periodontal disease is curable, determine whether or not periodontal disease is progressing, and the like.

In an exemplary embodiment saliva is employed as the specimen, however, there is no limitation thereto. For example, the specimen may be gingival crevicular fluid, dental plaque, a biofilm, a tongue coating, and the like. In particular using saliva as the specimen enables oral cavity information to be obtained for the specimen provider by a simple technique without damaging the gums or the like when taking the specimen.

Although the oral cavity microbiome (including base sequence reads of bacteria) has been given as an example of the oral cavity information detected from the specimen, there is no limitation thereto. In an exemplary embodiment the oral cavity information may be information related to a bacterial strain listed in the periodontal disease detection method (1) or (2), described below. Specific examples of information that may be utilized therefor include: a sum of branch lengths between bacteria in a phylogenetic tree (UniFrac distance); a number of reads (sequence and read quantity) obtained by next-generation sequencing; a type and quantity of inter-bacterial signaling (quorum sensing, autoinducer); a type and quantity of mutually syntrophic relationships between bacteria; bacterial growth conditions (oxygen demand, nutrient demand, etc.); a type and quantity of antigens affecting immune function; a type and quantity of protease for breaking down biological structures; a type and quantity of polynucleotides related to gene expression or gene control; a type and quantity of endotoxins and lipopolysaccharides configuring the outer membrane of cell walls of bacteria; a feature value expressing bacterial function; and the like. Each such information may be applied with a prescribed weighting and combined, or feature values may be obtained after characteristic extraction in main component analysis, and these then combined.

Although an example is given in which a value expressing a probability of periodontal disease contraction or a state of periodontal disease is a determination value based on a presence or absence of, or a proportion of, specific bacterial strains in the oral cavity microbiome, there is no limitation thereto. In an exemplary embodiment a determination value based on the presence or absence of, or the proportion of, a bacterial strain listed in the periodontal disease detection method (1) or (2), described below, may be employed.

The trained model may, as required, cause a computer to function so as to output a value expressing a probability of periodontal disease contraction or a state of periodontal disease based on the oral cavity information and other information. Examples of such other information include, for the specimen provider: the age, gender, smoking habits, and eating habits; a status of oral care implementation; a dental treatment history; a presence or absence of a chronic or pre-existing dental disorder and dental caries; a dental alignment; a volume of saliva; a state of oral cavity hygiene; a habit (such as bruxism, mouth-breathing, and the like); a state of stress; and the like.

There are no particular limitations to each of the configuration elements of the trained model of the present exemplary embodiment, and they may be the same as each of the configuration elements of any known trained model.

Data Structure

The data structure of the present exemplary embodiment is a data structure including oral cavity information detected from the specimen, and information identifying the specimen provider.

The data structure is employed in processing to compute a probability related to periodontal disease contraction or a state thereof using a trained model that has been pre-trained based on the oral cavity information detected from the specimen so as to output a value expressing a probability of periodontal disease contraction of the specimen provider or a state of periodontal disease.

The data structure may be employed to determine whether or not the specimen provider has contracted periodontal disease, determine whether or not periodontal disease is being cured, determine whether or not periodontal disease is curable, determine whether or not periodontal disease is progressing, and the like.

In an exemplary embodiment, saliva is employed as the specimen, however, there is no limitation thereto. For example, the specimen may be gingival crevicular fluid, dental plaque, a biofilm, a tongue coating, and the like. In particular using saliva as the specimen enables oral cavity information to be obtained for the specimen provider by a simple technique without damaging the gums or the like when taking the specimen.

Although the oral cavity microbiome (including base sequence reads of bacteria) has been given as an example of the oral cavity information detected from the specimen, there is no limitation thereto. In an exemplary embodiment the oral cavity information may be information related to a bacterial strain listed in the periodontal disease detection method (1) or (2), described below. Specific examples of information that may be utilized therefor include: a sum of branch lengths between bacteria in a phylogenetic tree (UniFrac distance); a number of reads (sequence and read quantity) obtained by next-generation sequencing; a type and quantity of inter-bacterial signaling (quorum sensing, autoinducer); a type and quantity of mutually syntrophic relationships between bacteria; bacterial growth conditions (oxygen demand, nutrient demand, etc.); a type and quantity of antigens affecting immune function; a type and quantity of protease for breaking down biological structures; a type and quantity of polynucleotides related to gene expression or gene control; a type and quantity of endotoxins and lipopolysaccharides configuring the outer membrane of cell walls of bacteria; a feature value expressing bacterial function; and the like. Each such information may be applied with a prescribed weighting and combined, or feature values may be obtained after characteristic extraction in main component analysis, and these then combined.

Although an example is given in which a value expressing a probability of periodontal disease contraction or a state of periodontal disease is a determination value based on a presence or absence of, or a proportion of, specific bacterial strains in the oral cavity microbiome, there is no limitation thereto. In an exemplary embodiment a determination value based on the presence or absence of a bacterial strain listed in the periodontal disease detection method (1) or (2), described below, or the proportion thereof, may be employed.

The data structure described above may, as required, be employed in processing to compute a probability related to periodontal disease contraction or a state thereof using a trained model that has been pre-trained based on the oral cavity information and other information so as to output a value expressing a probability of periodontal disease contraction or a state of periodontal disease. Examples of such other information include, for the specimen provider: the age, gender, smoking habits, and eating habits; a status of oral care implementation; a dental treatment history; a presence or absence of a chronic or pre-existing dental disorder and dental caries; a dental alignment; a volume of saliva; a state of oral cavity hygiene; a habit (such as bruxism, mouth-breathing, and the like); a state of stress; and the like.

There are no particular limitations to each of the configuration elements of the trained model of the present exemplary embodiment, and similar configuration elements of any known trained model may be employed therefor.

Operation of Machine Learning Device 100

On receipt of plural training data via the input section 10, the machine learning device 100 stores the plural training data in the training data storage section 30. The machine learning device 100 then executes a machine learning processing routine as illustrated in FIG. 2.

First, at step S100, for each of the plural training data, the function in its current state is employed to calculate based on the training data so as to calculate a reward for defined results of the probability of periodontal disease contraction or the state of periodontal disease.

Then at step S102, the function is updated so as to increase the reward based on the rewards calculated for each of the plural training data at step S100.

At step S104, determination is made as to whether or not a predetermined convergence condition has been satisfied, and processing returns to step S100 when the convergence condition has not been satisfied. However, processing transitions to step S106 when the convergence condition has been satisfied.

At step S106, the function as finally updated is stored in the trained model storage section 50, and then the training processing routine is ended.

Then when oral cavity information detected from the specimen is received as input of the determination subject via the input section 10, the determination section 60 of the machine learning device 100 takes the oral cavity information detected from the specimen input as the determination subject and uses the function as trained by the training section 40 to decide on at least one determination value selected from the group consisting of a probability of periodontal disease contraction and a state of periodontal disease for the specimen provider, and then outputs this determination value via the output section 90.

Periodontal Disease Detection Method (1)

The periodontal disease detection method of the present exemplary embodiment includes a detection process of detecting in the specimen at least two bacterial strains (hereafter also referred to as the detection target) selected from the group consisting of *Anaeroglobus, Cryptobacterium, Desulfobulbus, Desulfomicrobium, Desulfovibrio*, Erysipelotrichaceae, Fretibacterium, *Johnsonella, Mitsuokella*, Mollicutes, *Parascardovia, Pseudoramibacter, Pyramidobacter, Scardovia, Shuttleworthia*, and *Mycoplasma*.

Due to including the process of detecting at least two bacterial strains selected from these specific bacterial strains, the periodontal disease detection method of the present exemplary embodiment is a detection method having a raised precision of periodontal disease detection compared to cases in which determination is made based on the results of detecting a single bacterial strain alone. The technological concept of determining whether or not periodontal disease has been contracted by detecting plural strains from out of specific bacterial strains in the oral cavity has not hitherto either been described or suggested in prior art documents.

The detection method described above employed in determining whether or not the specimen provider has contracted periodontal disease, determining whether or not periodontal disease is being cured, determining whether or not periodontal disease is curable, determining whether or not periodontal disease is progressing, or the like.

Detection Process

The detection process may be performed by any method capable of detecting the detection target contained in the specimen. Examples of such a method include metagenomic analysis (such as 16S [rRNA] meta-analysis), immuno-chromatography, and gene amplification methods (such as realtime PCR, LAMP, or the like). In an exemplary embodiment the detection process is performed using metagenomic analysis. Metagenomic analysis is able to detect the presence or absence, and the proportional presence, of plural bacterial strains in a single process, which is advantageous from the perspective of detection efficiency compared to gene amplification methods that fundamentally detect a single bacterial strain in each process. The metagenomic analysis also has superior bacterial strain detection precision compared to qualitative immuno-chromatographic evaluations.

Specific examples of information that may be utilized as information detected include: a sum of branch lengths between bacteria in a phylogenetic tree (UniFrac distance); a number of reads (sequence and read quantity) obtained by next-generation sequencing; a type and quantity of inter-bacterial signaling (quorum sensing, autoinducer); a type and quantity of mutually syntrophic relationships between bacteria; bacterial growth conditions (oxygen demand, nutrient demand, etc.); a type and quantity of antigens affecting immune function; a type and quantity of protease for breaking down biological structures; a type and quantity of polynucleotides related to gene expression or gene control; a type and quantity of endotoxins and lipopolysaccharides configuring the outer membrane of cell walls of bacteria; a feature value expressing bacterial function; and the like. Each such information may be applied with a prescribed weighting and combined, or feature values may be obtained after characteristic extraction in main component analysis, and these then combined.

In an exemplary embodiment saliva is used as the specimen, however, there is no limitation thereto. For example, the specimen may be gingival crevicular fluid, dental plaque, a biofilm, a tongue coating, and the like. In particular using saliva as the specimen enables oral cavity information to be obtained for the specimen provider by a simple technique without damaging the gums or the like when taking the specimen.

From the perspective of improving detection precision, the detection target is at least two bacterial strains selected from the group consisting of *Anaeroglobus, Cryptobacterium, Desulfobulbus, Desulfomicrobium, Desulfovibrio,* Erysipelotrichaceae, Fretibacterium, *Johnsonella, Mitsuokella,* Mollicutes, *Parascardovia, Pseudoramibacter, Pyramidobacter, Scardovia, Shuttleworthia,* and *Mycoplasma,* is preferably at least three bacterial strains thereform, and is more preferably at least four bacterial strains thereform.

In an exemplary embodiment the detection target includes at least two bacterial strains selected from the group consisting of *Anaeroglobus,* Fretibacterium, and *Mycoplasma.*

Evaluation Process

The periodontal disease detection method of the present exemplary embodiment may include an evaluation process after the detection process to evaluate a possibility that a provider of the specimen has contracted periodontal disease based on the results obtained in the detection process. The evaluation process may be performed by any method capable of evaluating the possibility that the specimen provider has contracted periodontal disease based on the results obtained in the detection process. For example, a calculator may be employed therefor, or a color reaction or the like may be utilized therefor.

The evaluation process may include an analysis process to calculate a sum total of a number of bacteria contained in the specimen and a sum total of a number of detection target bacteria in the specimen, and may be evaluation performed based on the analysis results obtained by the analysis process.

In an exemplary embodiment the evaluation process evaluates the possibility that the specimen provider has contracted periodontal disease as high in cases in which a proportion of the sum total of the number of sequence reads of the detection target bacteria with respect to the sum total of the number of sequence reads obtained in the detection process is a proportion of a prescribed value or greater.

From the perspective of detection precision, the evaluation process preferably evaluates the possibility that the specimen provider has contracted periodontal disease as high in cases in which the sum total of the number of sequence reads of the detection target bacteria is 0.02% or greater with respect to the sum total of the number of sequence reads obtained in the detection process of 100%.

The "sum total of the number of sequence reads of the detection target bacteria" in the periodontal disease detection method of the present exemplary embodiment means the sum total of the number of sequence reads of bacteria of the two or more bacterial strains adopted as the detection target from out of the bacterial strains contained in the specimen, the two or more bacterial strains being bacterial strains included in the group consisting of *Anaeroglobus, Cryptobacterium, Desulfobulbus, Desulfomicrobium, Desulfovibrio,* Erysipelotrichaceae, Fretibacterium, *Johnsonella, Mitsuokella,* Mollicutes, *Parascardovia, Pseudoramibacter, Pyramidobacter, Scardovia, Shuttleworthia,* and *Mycoplasma.*

Thus the number of sequence reads of bacteria not adopted as the detection target are not included in the "sum total of the number of sequence reads of the detection target bacteria", even if they happen to be bacterial strains included in the above group.

In the evaluation process, the possibility that the specimen provider has contracted periodontal disease may be evaluated, as required, with reference to other information in addition to the results obtained by the detection process.

Examples of such other information include, for the specimen provider: the age, gender, smoking habits, and eating habits; a status of oral care implementation; a dental treatment history; a presence or absence of a chronic or pre-existing dental disorder and dental caries; a dental alignment; a volume of saliva; a state of oral cavity hygiene; a habit (such as bruxism, mouth-breathing, and the like); a state of stress; and the like.

Periodontal Disease Detection System (1)

A periodontal disease detection system of the present exemplary embodiment includes a detection section to detect in the specimen at least two bacterial strains (a detection target) selected from the group consisting of *Anaeroglobus, Cryptobacterium, Desulfobulbus, Desulfomicrobium, Desulfovibrio,* Erysipelotrichaceae, Fretibacterium, *Johnsonella, Mitsuokella*, Mollicutes, *Parascardovia, Pseudoramibacter, Pyramidobacter, Scardovia, Shuttleworthia*, and *Mycoplasma*.

The detection system described above may be used to determine whether or not the specimen provider has contracted periodontal disease, determine whether or not periodontal disease is being cured, determine whether or not periodontal disease is curable, determine whether or not periodontal disease is progressing, and the like.

Detection Section

The detection section is not particularly limited as long as it is able to detect the detection target contained in the specimen. Examples of the detection section include devices that execute metagenomic analysis (such as 16S meta-analysis), immuno-chromatography, and gene amplification methods (such as realtime PCR, LAMP, or the like). In an exemplary embodiment a detection process is performed by metagenomic analysis. Metagenomic analysis is able to detect the presence or absence, and the proportional presence, of plural bacterial strains in a single process, which is advantageous from the perspective of detection efficiency compared to gene amplification methods that fundamentally detect a single bacterial strain in each process. The metagenomic analysis also has superior bacterial strain detection precision compared to qualitative immuno-chromatographic evaluations.

Specific examples of information that may be utilized as information detected include: a sum of branch lengths between bacteria in a phylogenetic tree (UniFrac distance); a number of reads (sequence and read quantity) obtained by next-generation sequencing; a type and quantity of inter-bacterial signaling (quorum sensing, autoinducer); a type and quantity of mutually syntrophic relationships between bacteria; bacterial growth conditions (oxygen demand, nutrient demand, etc.); a type and quantity of antigens affecting immune function; a type and quantity of protease for breaking down biological structures; a type and quantity of polynucleotides related to gene expression or gene control; a type and quantity of endotoxins and lipopolysaccharides configuring the outer membrane of cell walls of bacteria; a feature value expressing bacterial function; and the like. Each such information may be applied with a prescribed weighting and combined, or feature values may be obtained after characteristic extraction in main component analysis, and these then combined.

There are no particular limitations to the specific configuration of the detection section, and a detection section may be selected according to the detection method adopted. For example, a detection section may be employed that executes detection with a calculator such as a computer or the like, or a detection section may be employed that executes detection through a technique such as a test strip.

An exemplary embodiment uses saliva as the specimen, however, there is no limitation thereto. For example, the specimen may be gingival crevicular fluid, dental plaque, a biofilm, a tongue coating, and the like. In particular using saliva as the specimen enables oral cavity information to be obtained for the specimen provider by a simple technique without damaging the gums or the like when taking the specimen.

From the perspective of improving detection precision, the detection target is at least two bacterial strains selected from the group consisting of *Anaeroglobus, Cryptobacterium, Desulfobulbus, Desulfomicrobium, Desulfovibrio*, Erysipelotrichaceae, Fretibacterium, *Johnsonella, Mitsuokella*, Mollicutes, *Parascardovia, Pseudoramibacter, Pyramidobacter, Scardovia, Shuttleworthia*, and *Mycoplasma*, is preferably at least three bacterial strains selected therefrom, and is more preferably at least four bacterial strains selected therefrom.

In an exemplary embodiment the detection target includes at least two bacterial strains selected from the group consisting of *Anaeroglobus*, Fretibacterium, and *Mycoplasma*.

Evaluation Section

The periodontal disease detection system of the present exemplary embodiment may include an evaluation section to evaluate the possibility that the specimen provider has contracted periodontal disease based on the results obtained by the detection section. The evaluation section is not particularly limited as long as it is able to evaluate the possibility that the specimen provider has contracted periodontal disease based on the results obtained by the detection section. For example, a calculator may be employed therefor, or a color reaction or the like may be utilized therefor.

The evaluation section may include an analysis section to calculate a sum total of a number of sequence reads obtained in the detection process and a sum total of a number of sequence reads of the detection target bacteria obtained in the detection process, and perform evaluation based on the analysis results obtained by the analysis section.

In an exemplary embodiment the evaluation section evaluates the possibility that the specimen provider has contracted periodontal disease as high in cases in which a proportion of a sum total of the number of sequence reads of the detection target bacteria with respect to the sum total of the number of sequence reads obtained in the detection section is a proportion of a prescribed value or greater.

From the perspective of detection precision, the evaluation section preferably evaluates the possibility that the specimen provider has contracted periodontal disease as high in cases in which the sum total of the number of sequence reads of the detection target bacteria is 0.02% or greater with respect to the sum total of the number of sequence reads obtained in the detection process of 100%.

In the periodontal disease detection system of the present exemplary embodiment, the "sum total of the number of sequence reads of the detection target bacteria" means the sum total of the number of sequence reads of the two or more bacterial strains adopted as the detection target from out of the bacterial strains contained in the specimen, the two or more bacterial strains being bacterial strains included in the group consisting of *Anaeroglobus, Cryptobacterium, Desulfobulbus, Desulfomicrobium, Desulfovibrio*, Erysipelotrichaceae, Fretibacterium, *Johnsonella, Mitsuokella*, Mollicutes, *Parascardovia, Pseudoramibacter, Pyramidobacter, Scardovia, Shuttleworthia*, and *Mycoplasma*.

Thus the number of [sequence reads of] bacteria not adopted as the detection target are not included in the "sum total of the number of sequence reads of the detection target bacteria", even if they happen to be bacterial strains included in the above group.

The periodontal disease detection system of the present exemplary embodiment may include a section where another function is exhibited, in addition to the detection section described above, and the evaluation section and the analysis section, which are included as required. Moreover, the periodontal disease detection system of the present exemplary embodiment may be embodied by a state in which each of the sections described above are integrated together in a single device, or may be embodied by a combination of devices equipped with each of the sections. The periodontal disease detection system of the present exemplary embodiment also encompasses a more simplified embodiment (such as the periodontal disease detection kit described below).

Periodontal Disease Detection Kit (1)

The periodontal disease detection kit of the present exemplary embodiment includes a detection device to detect in the specimen at least two bacterial strains (a detection target) selected from the group consisting of *Anaeroglobus, Cryptobacterium, Desulfobulbus, Desulfomicrobium, Desulfovibrio,* Erysipelotrichaceae, Fretibacterium, *Johnsonella, Mitsuokella,* Mollicutes, *Parascardovia, Pseudoramibacter, Pyramidobacter, Scardovia, Shuttleworthia,* and *Mycoplasma.*

The detection device is not particularly limited as long as it is capable of detecting the detection target contained in the specimen. The detection device may, for example, be mounted as the detection section to the periodontal disease detection system described above. Moreover, the detection device may, as required, include devices that exhibit another functions other than evaluation and analysis.

In cases in which the periodontal disease detection kit includes such devices, these devices may be in an integrated state to the detection device (including cases in which the detection device also exhibits the functionality of these devices), or these devices may be a combination of separate devices.

Periodontal Disease Diagnostic Method (1)

The periodontal disease diagnostic method of the present exemplary embodiment includes a process to diagnose whether or not the specimen provider has contracted periodontal disease based on information as to whether or not at least two bacterial strains (hereafter also referred to as the detection target) selected from the group consisting of *Anaeroglobus, Cryptobacterium, Desulfobulbus, Desulfomicrobium, Desulfovibrio,* Erysipelotrichaceae, Fretibacterium, *Johnsonella, Mitsuokella,* Mollicutes, *Parascardovia, Pseudoramibacter, Pyramidobacter, Scardovia, Shuttleworthia,* and *Mycoplasma* have been detected in the specimen.

In an exemplary embodiment saliva is used as the specimen, however, there is no limitation thereto. For example, the specimen may be gingival crevicular fluid, dental plaque, a biofilm, a tongue coating, and the like. In particular using saliva as the specimen enables oral cavity information to be obtained for the specimen provider by a simple technique without damaging the gums or the like when taking the specimen.

In the method described above, diagnosing whether or not the specimen provider has contracted periodontal disease encompasses, in addition to cases in which whether or not the specimen provider has certainly contracted periodontal disease is diagnosed, cases in which a state of progression of periodontal disease is diagnosed when the specimen provider has contracted periodontal disease, cases in which the possibility the specimen provider has contracted periodontal disease (or will contract periodontal disease in the future) is diagnosed, and the like. Furthermore, it also encompasses cases in which whether or not periodontal disease is being cured is diagnosed, whether or not periodontal disease is curable is diagnosed, whether or not periodontal disease is progressing is diagnosed, and the like.

In the method described above the method to obtain information about whether or not the detection target has been detected in the specimen is not particularly limited. For example, the information obtained by the techniques described in the periodontal disease detection method or the periodontal disease detection system described above may be obtained thereby. The details of each of the exemplary embodiments described above may also be applied in the present method.

Periodontal Disease Detection Method (2)

The periodontal disease detection method of the present exemplary embodiment includes a detection process to detect in the specimen at least one bacterial strain (also referred to below as detection target) selected from the group consisting of GN02, *Ottowia, Sneathia,* and *Lautropia.*

A discovery made by comparing specimens taken from providers who have not contracted periodontal disease against specimens taken from providers who have contracted periodontal disease, is that there tends to be more of at least one bacterial strain selected from the group consisting of GN02, *Ottowia, Sneathia,* and *Lautropia* contained in a specimen from a provider who has not contracted periodontal disease than in a specimen from a provider who has contracted periodontal disease. The periodontal disease detection method of the present exemplary embodiment is based on this discovery.

The detection method described above may be employed to determine whether or not the specimen provider has contracted periodontal disease, determine whether or not periodontal disease is being cured, determine whether or not periodontal disease is curable, determine whether or not periodontal disease is progressing, and the like.

Detection Process

The detection process may be performed by any method capable of detecting the detection target contained in the specimen. Examples thereof include metagenomic analysis (such as 16S meta-analysis), immuno-chromatography, and gene amplification methods (such as realtime PCR, LAMP, or the like). In an exemplary embodiment the detection process is performed by metagenomic analysis. Metagenomic analysis is able to detect the presence or absence, and the proportional presence, of plural bacterial strains in a single process, which is advantageous from the perspective of detection efficiency compared to gene amplification methods that fundamentally detect a single bacterial strain in each process. The metagenomic analysis also has superior bacterial strain detection precision compared to qualitative immuno-chromatographic evaluations.

Specific examples of information that may be utilized as information detected include: a sum of branch lengths between bacteria in a phylogenetic tree (UniFrac distance); a number of reads (sequence and read quantity) obtained by next-generation sequencing; a type and quantity of inter-bacterial signaling (quorum sensing, autoinducer); a type and quantity of mutually syntrophic relationships between bacteria; bacterial growth conditions (oxygen demand, nutrient demand, etc.); a type and quantity of antigens affecting immune function; a type and quantity of protease for breaking down biological structures; a type and quantity of polynucleotides related to gene expression or gene control; a type and quantity of endotoxins and lipopolysaccharides configuring the outer membrane of cell walls of bacteria; a feature value expressing bacterial function; and the like.

Each such information may be applied with a prescribed weighting and combined, or feature values may be obtained after characteristic extraction in main component analysis, and these then combined.

An exemplary embodiment uses saliva as the specimen, however, there is no limitation thereto. For example, the specimen may be gingival crevicular fluid, dental plaque, a biofilm, a tongue coating, and the like. In particular using saliva as the specimen enables oral cavity information to be obtained for the specimen provider by a simple technique without damaging the gums or the like when taking the specimen.

From the perspective of improving detection precision, the detection target is at least one bacterial strain selected from the group consisting of GN02, *Ottowia, Sneathia*, and *Lautropia*, is preferably at least two bacterial strains thereof, and is more preferably at least three bacterial strains thereof.

The detection target preferably includes at least *Lautropia*, and is more preferably a combination of *Lautropia* combined with at least one bacterial strain selected from the group consisting of N02, *Ottowia*, and *Sneathia*.

Evaluation Process

The periodontal disease diagnostic method of the present exemplary embodiment may include an evaluation process after the detection process to evaluate the possibility that the specimen provider has contracted periodontal disease based on the results obtained in the detection process. The evaluation process may be performed by any method capable of evaluating the possibility that the specimen provider has contracted periodontal disease based on the results obtained in the detection process. For example, a calculator may be employed therefor, or a color reaction or the like may be utilized therefor.

The evaluation process may include an analysis process to calculate a sum total of a number of sequence reads (reads) obtained in the detection process and a sum total of a number of sequence reads of the detection target bacteria obtained in the detection process, and may be evaluation performed based on the analysis results obtained by the analysis process.

In an exemplary embodiment the evaluation process evaluates the possibility that the specimen provider has contracted periodontal disease as high in cases in which a proportion of the sum total of the number of sequence reads of the detection target bacteria with respect to the sum total of the number of sequence reads obtained in the detection process is a proportion of a prescribed value or less.

From the perspective of detection precision, the evaluation process preferably evaluates the possibility that the specimen provider has contracted periodontal disease as high in cases in which the sum total of the number of sequence reads of the detection target bacteria is 0.01% or less with respect to the sum total of the number of sequence reads obtained in the detection process of 100%.

In the periodontal disease detection method of the present exemplary embodiment the "sum total of the number of sequence reads of the detection target bacteria" means the sum total of the number of sequence reads of the one or more bacterial strains adopted as the detection target from out of the bacterial strains contained in the specimen, wherein the one or more bacterial strains are bacterial strains included in the group consisting of GN02, *Ottowia, Sneathia*, and *Lautropia*.

Thus the number of sequence reads of bacteria not adopted as the detection target are not included in the "sum total of the number of sequence reads of the detection target bacteria", even if they happen to be bacterial strains included in the above group.

In the evaluation process, the possibility that the specimen provider has contracted periodontal disease may be evaluated, as required, with reference to other information in addition to the results obtained by the detection process.

Examples of such other information include, for the specimen provider: the age, gender, smoking habits, and eating habits; a status of oral care implementation; a dental treatment history; a presence or absence of a chronic or pre-existing dental disorder and dental caries; a dental alignment; a volume of saliva; a state of oral cavity hygiene; a habit (such as bruxism, mouth-breathing, and the like); a state of stress; and the like.

Periodontal Disease Detection System (2)

The periodontal disease detection system of the present exemplary embodiment includes a detection section to detect in the specimen at least one bacterial strain (a detection target) selected from the group consisting of GN02, *Ottowia, Sneathia*, and *Lautropia*.

The detection system described above may be employed to determine whether or not the specimen provider has contracted periodontal disease, determine whether or not periodontal disease is being cured, determine whether or not periodontal disease is curable, determine whether or not periodontal disease is progressing, and the like.

Detection Section

The detection section is not particularly limited as long as it is capable of detecting the detection target contained in the specimen. Examples thereof include devices that execute metagenomic analysis (such as 16S meta-analysis), immuno-chromatography, and gene amplification methods (such as realtime PCR, LAMP, or the like). In an exemplary embodiment the detection process is performed by metagenomic analysis. Metagenomic analysis is able to detect the presence or absence, and the proportional presence, of plural bacterial strains in a single process, which is advantageous from the perspective of detection efficiency compared to gene amplification methods that fundamentally detect a single bacterial strain in each process. The metagenomic analysis also has superior bacterial strain detection precision compared to qualitative immuno-chromatographic evaluations.

Specific examples of information that may be utilized as information detected include: a sum of branch lengths between bacteria in a phylogenetic tree (UniFrac distance); a number of reads (sequence and read quantity) obtained by next-generation sequencing; a type and quantity of inter-bacterial signaling (quorum sensing, autoinducer); a type and quantity of mutually syntrophic relationships between bacteria; bacterial growth conditions (oxygen demand, nutrient demand, etc.); a type and quantity of antigens affecting immune function; a type and quantity of protease for breaking down biological structures; a type and quantity of polynucleotides related to gene expression or gene control; a type and quantity of endotoxins and lipopolysaccharides configuring the outer membrane of cell walls of bacteria; a feature value expressing bacterial function; and the like. Each such information may be applied with a prescribed weighting and combined, or feature values may be obtained after characteristic extraction in main component analysis, and these then combined.

The specific configuration of the detection section is not particularly limited, and the detection section may be selected according to the detection method adopted. For example, a detection section may be employed that executes detection with a calculator such as a computer or the like, or a detection section may be employed that executes detection through a technique such as a test strip.

In an exemplary embodiment saliva is used as the specimen, however, there is no limitation thereto. For example, the specimen may be gingival crevicular fluid, dental plaque, a biofilm, a tongue coating, and the like. In particular using saliva as the specimen enables oral cavity information to be obtained for the specimen provider by a simple technique without damaging the gums or the like when taking the specimen.

From the perspective of improving detection precision, the detection target is at least one bacterial strain selected from the group consisting of GN02, *Ottowia, Sneathia,* and *Lautropia,* is preferably at least two bacterial strains thereof, and is more preferably at least three bacterial strains thereof. The detection target moreover preferably includes at least *Lautropia*.

The detection target preferably includes at least *Lautropia,* and is more preferably a combination of *Lautropia* combined with at least one bacterial strain selected from the group consisting of GN02, *Ottowia,* and *Sneathia*.

Evaluation Section

The periodontal disease detection system of the present exemplary embodiment may include an evaluation section to evaluate the possibility that the specimen provider has contracted periodontal disease based on the results obtained by the detection section. The evaluation section is not particularly limited as long as it is able to evaluate the possibility that the specimen provider has contracted periodontal disease based on the results obtained by the detection section. For example, a calculator may be employed therefor, or a color reaction or the like may be utilized therefor.

The evaluation section may include an analysis section to calculate a sum total of a number of sequence reads obtained in the detection process and a sum total of a number of sequence reads of the detection target bacteria obtained in the detection process, and perform evaluation based on the analysis results obtained by the analysis section.

In an exemplary embodiment the evaluation section evaluates the possibility that the specimen provider has contracted periodontal disease as high in cases in which a proportion of a sum total of the number of sequence reads of the detection target bacteria with respect to the sum total of the number of sequence reads obtained in the detection section is a proportion of a prescribed value or less.

From the perspective of detection precision, the evaluation section preferably evaluates the possibility that the specimen provider has contracted periodontal disease as high in cases in which the sum total of the number of sequence reads of the detection target bacteria is 0.01% or less with respect to the sum total of the number of sequence reads obtained in the detection process of 100%.

In the periodontal disease detection system of the present exemplary embodiment the "sum total of the number of sequence reads of the detection target bacteria" means the sum total of the number of sequence reads of the one or more bacterial strains adopted as the detection target from out of the bacterial strains contained in the specimen, wherein the one or more bacterial strains are bacterial strains included in the group consisting of GN02, *Ottowia, Sneathia,* and *Lautropia*.

Thus the number of [sequence reads of] bacteria not adopted as the detection target are not included in the "sum total of the number of sequence reads of the detection target bacteria", even if they happen to be bacterial strains included in the above group.

The periodontal disease detection system of the present exemplary embodiment may include a section where another function is exhibited, in addition to the detection section described above, and the evaluation section and the analysis section, which are included as required. Moreover, the periodontal disease detection system of the present exemplary embodiment may be embodied by a state in which each of the sections described above are integrated together in a single device, or may be embodied by a combination of devices equipped with each of the sections. The periodontal disease detection system of the present exemplary embodiment also encompasses a more simplified embodiment (such as the periodontal disease detection kit described below).

Periodontal Disease Detection Kit (2)

The periodontal disease detection kit of the present exemplary embodiment includes a detection device to detect in the specimen at least one bacterial strain (a detection target) selected from the group consisting of GN02, *Ottowia, Sneathia,* and *Lautropia*.

The detection device is not particularly limited as long as it is capable of detecting the detection target contained in the specimen. The detection device may, for example, be mounted as the detection section to the periodontal disease detection system described above. Moreover, the detection device may, as required, include devices that exhibit another functions other than evaluation and analysis.

In cases in which the periodontal disease detection kit includes such devices, these devices may be in an integrated state to the detection device (including cases in which the detection device also exhibits the functionality of these devices), or these devices may be a combination of separate devices.

Periodontal Disease Diagnostic Method (2)

The periodontal disease diagnostic method of the present exemplary embodiment includes a process to diagnose whether or not the specimen provider has contracted periodontal disease based on information as to whether or not at least one bacterial strain (a detection target) selected from the group consisting of GN02, *Ottowia, Sneathia,* and *Lautropia* has been detected in the specimen.

In an exemplary embodiment saliva is used as the specimen, however, there is no limitation thereto. For example, the specimen may be gingival crevicular fluid, dental plaque, a biofilm, a tongue coating, and the like. In particular using saliva as the specimen enables oral cavity information to be obtained for the specimen provider by a simple technique without damaging the gums or the like when taking the specimen.

In the method described above, diagnosing whether or not the specimen provider has contracted periodontal disease encompasses, in addition to cases in which whether or not the specimen provider has certainly contracted periodontal disease is diagnosed, cases in which a state of progression of periodontal disease is diagnosed when the specimen provider has contracted periodontal disease, cases in which the possibility the specimen provider has contracted periodontal disease (or will contract periodontal disease in the future) is diagnosed, and the like. Furthermore, it also encompasses cases in which whether or not periodontal disease is being cured is diagnosed, whether or not periodontal disease is curable is diagnosed, whether or not periodontal disease is progressing is diagnosed, and the like.

In the method described above the method to obtain information about whether or not the detection target has been detected in the specimen is not particularly limited. For example, the information obtained by the techniques described in the periodontal disease detection method or the periodontal disease detection system described above may be obtained thereby. The details of each of the exemplary embodiments described above may also be applied in the present method.

EXAMPLES

The above exemplary embodiments will now be explained by way of specific Examples, however, the above exemplary embodiments are not limited by these Examples.

Example 1

Saliva was taken from test subjects A1 to A10 who had contracted periodontal disease (who had a location where the periodontal pocket was 5 mm or greater), and from test subjects B1 to B8 who had not contracted periodontal disease (who had healthy periodontal tissue in the jaw overall, irrespective of whether or not there was any mild gingivitis). Detection target bacterial strains were then detected in the saliva using the following procedure.

Detection Method

Bacterial genome DNA was extracted from the saliva, and amplification was performed by PCR (SimpliAmp, by Thermo Fisher Scientific Inc.) using primers (V3-V4 or V4) containing region specific sequences for the 16SrDNA region of V3-V4 region (F:5'-CCTACGGG-NGGCWGCAG-3', R:5'-GACTACHVGGGTATCT-AATCC-3') or V4 region (F:5'-GTGCCAGCM-GCCGCGGTAA-3', R:5'-GGACTACHVGGGTWT-CTAAT-3'). Adaptor sequences and index sequences were attached to the amplified PCR fragments to construct a library. The library was then introduced to a next-generation sequencer MiSeq (by Illumina Inc.) to acquire base sequence reads (reads).

Next a computer was employed to perform a comparison between the acquired sequences and bacterial genome databases (public database 16SMicrobial, NCBI, and the like) using BLAST so as to elucidate the microbiome from the number of sequence reads (reads) (16S meta-analysis). Next the proportions (%) were computed for the number of sequence reads of the individual bacterial strains for the 16 strains listed in Table 1, or the number of sequence reads of plural combinations thereof, with respect to the sum total of the number of sequence reads obtained in the detection results.

The protocol underlying the method described above can be referenced at the following URL: https://support.illumina.com/content/dam/illumina-support/documents/documentation/chemistry_documentation/16s/16s-metagenomic-library-prep-guide-15044223-b.pdf The proportions (%) obtained for the number of sequence reads of the bacterial strains for the 16 strains detected as described above are listed in Table 1. In Table 1 "A+F" represents the sum total of the number of sequence reads of *Anaeroglobus* and Fretibacterium, "A+F+M" represents the sum total of the number of sequence reads of *Anaeroglobus*, Fretibacterium, and *Mycoplasma*, and "All" represents the sum total of the number of sequence reads for all the 16 strains listed in the table.

TABLE 1

| | Test Subject | | | | | | | | | |
|---|---|---|---|---|---|---|---|---|---|---|
| | A1 | A2 | A3 | A4 | A5 | A6 | A7 | A8 | A9 | A10 |
| *Anaeroglobus* | 0.0329 | 0.0398 | 0.1098 | 0.0671 | 0.1055 | 0.0084 | 0.5564 | 0.0799 | 0.0101 | 0.3073 |
| *Cryptobacterium* | 0.0000 | 0.0000 | 0.0242 | 0.0000 | 0.0066 | 0.0084 | 0.0229 | 0.0092 | 0.0029 | 0.0000 |
| *Desulfobulbus* | 0.0058 | 0.0596 | 0.0000 | 0.0328 | 0.0000 | 0.0000 | 0.0556 | 0.0000 | 0.0029 | 0.0078 |
| *Desulfomicrobium* | 0.0290 | 0.1889 | 0.0502 | 0.0000 | 0.0088 | 0.0000 | 0.0000 | 0.5042 | 0.2407 | 0.0000 |
| *Desulfovibrio* | 0.0000 | 0.0000 | 0.0000 | 0.0000 | 0.0000 | 0.0000 | 0.0000 | 0.0830 | 0.0375 | 0.0497 |
| Erysipelotrichaceae | 0.0000 | 0.0000 | 0.0000 | 0.0000 | 0.0044 | 0.0000 | 0.0442 | 0.0061 | 0.0029 | 0.1195 |
| *Fretibacterium* | 0.1897 | 0.1392 | 0.0465 | 0.3370 | 0.0044 | 0.1822 | 0.5352 | 0.3874 | 0.2306 | 0.0729 |
| *Johnsonella* | 0.0523 | 0.0497 | 0.0428 | 0.0075 | 0.0000 | 0.0000 | 0.0155 | 0.0861 | 0.0317 | 0.0078 |
| *Mitsuokella* | 0.0000 | 0.0000 | 0.0837 | 0.0030 | 0.0044 | 0.0000 | 0.2659 | 0.0000 | 0.0072 | 0.0140 |
| Mollicutes | 0.0194 | 0.0000 | 0.0558 | 0.0000 | 0.0000 | 1.5543 | 0.0000 | 0.0307 | 0.1369 | 0.0078 |
| *Parascardovia* | 0.0000 | 0.0000 | 0.0000 | 0.0000 | 0.0000 | 0.0000 | 0.0957 | 0.0061 | 0.0029 | 0.0171 |
| Pseudoramibacter | 0.0039 | 0.0994 | 0.0000 | 0.0239 | 0.0000 | 0.0063 | 0.0254 | 0.0215 | 0.0072 | 0.0000 |
| Pyramidobacter | 0.0000 | 0.0000 | 0.0000 | 0.0000 | 0.0000 | 0.0084 | 1.6702 | 0.0000 | 0.0000 | 0.0698 |
| *Scardovia* | 0.0000 | 0.1292 | 0.3982 | 0.0000 | 0.0176 | 0.0042 | 0.4411 | 0.0523 | 0.2017 | 0.0559 |
| *Shuttleworthia* | 0.0000 | 0.0000 | 0.0186 | 0.0134 | 0.0242 | 0.0000 | 0.0466 | 0.0000 | 0.0086 | 0.0140 |
| *Mycoplasma* | 5.3451 | 2.2567 | 0.349 | 0.5531 | 0.0176 | 0.4546 | 0.0000 | 0.7901 | 0.6730 | 0.1257 |

TABLE 1-continued

| | | | | | | | | | | |
|---|---|---|---|---|---|---|---|---|---|---|
| A + F | 0.2226 | 0.1789 | 0.1563 | 0.4040 | 0.1099 | 0.1906 | 1.0916 | 0.4673 | 0.2407 | 0.3802 |
| A + F + M | 5.5677 | 2.4356 | 0.5061 | 0.9572 | 0.1275 | 0.6452 | 1.0916 | 1.2574 | 0.9136 | 0.5060 |
| All | 5.6781 | 2.9625 | 1.1796 | 1.0377 | 0.1934 | 2.2267 | 3.7748 | 2.0568 | 1.5967 | 0.8691 |

| | Test Subject | | | | | | | |
|---|---|---|---|---|---|---|---|---|
| | B1 | B2 | B3 | B4 | B5 | B6 | B7 | B8 |
| Anaeroglobus | 0.0000 | 0.0000 | 0.0000 | 0.0000 | 0.0000 | 0.0000 | 0.0000 | 0.0000 |
| Cryptobacterium | 0.0000 | 0.0000 | 0.0000 | 0.0000 | 0.0000 | 0.0000 | 0.0000 | 0.0000 |
| Desulfobulbus | 0.0000 | 0.0000 | 0.0000 | 0.0000 | 0.0000 | 0.0000 | 0.0000 | 0.0000 |
| Desulfomicrobium | 0.0000 | 0.0000 | 0.0000 | 0.0000 | 0.0000 | 0.0000 | 0.0000 | 0.0000 |
| Desulfovibrio | 0.0000 | 0.0000 | 0.0000 | 0.0000 | 0.0000 | 0.0000 | 0.0000 | 0.0000 |
| Erysipelotrichaceae | 0.0000 | 0.0000 | 0.0000 | 0.0000 | 0.0000 | 0.0000 | 0.0000 | 0.0000 |
| Fretibacterium | 0.0000 | 0.0000 | 0.0000 | 0.0000 | 0.0000 | 0.0000 | 0.0000 | 0.0042 |
| Johnsonella | 0.0000 | 0.0000 | 0.0000 | 0.0000 | 0.0129 | 0.0000 | 0.0000 | 0.0000 |
| Mitsuokella | 0.0000 | 0.0000 | 0.0000 | 0.0000 | 0.0000 | 0.0000 | 0.0000 | 0.0000 |
| Mollicutes | 0.0000 | 0.0000 | 0.0000 | 0.0000 | 0.0000 | 0.0000 | 0.0000 | 0.0000 |
| Parascardovia | 0.0000 | 0.0000 | 0.0000 | 0.0000 | 0.0000 | 0.0000 | 0.0000 | 0.0000 |
| Pseudoramibacter | 0.0000 | 0.0000 | 0.0000 | 0.0000 | 0.0000 | 0.0000 | 0.0000 | 0.0000 |
| Pyramidobacter | 0.0000 | 0.0000 | 0.0000 | 0.0000 | 0.0000 | 0.0000 | 0.0000 | 0.0000 |
| Scardovia | 0.0000 | 0.0000 | 0.0000 | 0.0000 | 0.0000 | 0.0047 | 0.0000 | 0.0000 |
| Shuttleworthia | 0.0000 | 0.0000 | 0.0000 | 0.0000 | 0.0000 | 0.0000 | 0.0000 | 0.0000 |
| Mycoplasma | 0.0000 | 0.0000 | 0.0000 | 0.0191 | 0.0000 | 0.0000 | 0.0144 | 0.0000 |
| A + F | 0.0000 | 0.0000 | 0.0000 | 0.0000 | 0.0000 | 0.0000 | 0.0000 | 0.0042 |
| A + F + M | 0.0000 | 0.0000 | 0.0000 | 0.0191 | 0.0000 | 0.0000 | 0.0144 | 0.0042 |
| All | 0.0000 | 0.0000 | 0.0000 | 0.0191 | 0.0129 | 0.0047 | 0.0144 | 0.0042 |

Detection Result Review

In cases in which two bacterial strains (*Anaeroglobus* and *Fretibacterium*) were adopted as the detection target, the test subject group who had contracted periodontal disease had a sum total of the number of sequence reads thereof that exceeded 0.02% of the sum total of the number of sequence reads detected. However, in cases in which the two bacterial strains (*Anaeroglobus* and *Fretibacterium*) were adopted as the detection target, the test subject group who had not contracted periodontal disease had a sum total of the number of sequence reads thereof of under 0.02% of the sum total of the number of sequence reads detected.

In cases in which three bacterial strains (*Anaeroglobus*, *Fretibacterium*, and *Mycoplasma*) were adopted as the detection target, the test subject group who had contracted periodontal disease had a sum total of the number of sequence reads thereof that exceeded 0.02% of the sum total of the number of sequence reads detected. However, in cases in which the three bacterial strains (*Anaeroglobus*, *Fretibacterium*, and *Mycoplasma*) were adopted as the detection target, the test subject group who had not contracted periodontal disease had a sum total of the number of sequence reads thereof of under 0.02% of the sum total of the number of sequence reads detected.

When 16 bacterial strains (*Anaeroglobus*, *Cryptobacterium*, *Desulfobulbus*, *Desulfomicrobium*, *Desulfovibrio*, Erysipelotrichaceae, *Fretibacterium*, *Johnsonella*, *Mitsuokella*, Mollicutes, *Parascardovia*, *Pseudoramibacter*, *Pyramidobacter*, *Scardovia*, *Shuttleworthia*, and *Mycoplasma*) were adopted as the detection target, the test subject group who had contracted periodontal disease had a sum total of the number of sequence reads thereof that exceeded 0.02% of the sum total of the number of sequence reads detected. However, when the 16 bacterial strains (*Anaeroglobus*, *Cryptobacterium*, *Desulfobulbus*, *Desulfomicrobium*, *Desulfovibrio*, Erysipelotrichaceae, *Fretibacterium*, *Johnsonella*, *Mitsuokella*, Mollicutes, *Parascardovia*, *Pseudoramibacter*, *Pyramidobacter*, *Scardovia*, *Shuttleworthia*, and *Mycoplasma*) were adopted as the detection target, the test subject group who had not contracted periodontal disease had a sum total of the number of sequence reads thereof of under 0.02% of the sum total of the number of sequence reads detected.

*Fretibacterium* was detected in the saliva of the test subject B8, a member of the test subject group that had not contracted periodontal disease, and the proportion thereof was similar to that of the test subject A5 who had contracted periodontal disease. This result indicates that whether or not periodontal disease has been contracted cannot always be determined from the individual detection result of *Fretibacterium* in the saliva, and this implies that utilizing the detection results of plural bacterial strains conceivably has superior detection precision thereto.

It is apparent from the above results that the periodontal disease diagnostic method including the process to detect in the specimen at least two bacterial strains selected from the group consisting of *Anaeroglobus*, *Cryptobacterium*, *Desulfobulbus*, *Desulfomicrobium*, *Desulfovibrio*, Erysipelotrichaceae, *Fretibacterium*, *Johnsonella*, *Mitsuokella*, Mollicutes, *Parascardovia*, *Pseudoramibacter*, *Pyramidobacter*, *Scardovia*, *Shuttleworthia*, and *Mycoplasma* is useful in the evaluation of the possibility that the specimen provider has contracted periodontal disease.

Example 2

Saliva was taken from test subjects C1 to C9 who had not contracted periodontal disease (who has no inflammation of the gums), and from test subjects D1 to D8 who had contracted periodontal disease (who had a location where the periodontal pocket was 6 mm or greater). Detection target bacterial strains were then detected in the saliva similarly to in Example 1, and the proportions (%) were computed of the number of sequence reads of the individual bacterial strains for the four strains listed in Table 1, or the number of sequence reads of plural combinations thereof, with respect to the sum total of the number of sequence reads obtained in the detection results.

The proportions (%) obtained of the number of sequence reads for the four bacterial strains detected as described above are listed in Table 1. In Table 1 "O+S" represents the sum total of the number of sequence reads of *Ottowia* and *Sneathia*, "L+S" represents the sum total of the number of sequence reads of *Lautropia* and *Sneathia*, and "All" represents the sum total of the number of sequence reads of the four strains listed in the table.

subject group who had not contracted periodontal disease had a sum total of the number of sequence reads thereof that in each case exceeded 0.01% of the sum total of the number of sequence reads detected. However, in cases in which the two bacterial strains of *Ottowia* and *Sneathia*, or in cases in which the two bacterial strains of *Lautropia* and *Sneathia*, were adopted as the detection target, the test subject group who had contracted periodontal disease had a sum total thereof that in each case did not exceed 0.01% of the sum total of the number of sequence reads detected.

When four bacterial strains of GN02, *Ottowia*, *Sneathia*, and *Lautropia* were adopted as the detection target, the test subject group who had not contracted periodontal disease had a sum total of the number of sequence reads thereof that exceeded 0.01% of the sum total of the number of sequence reads detected. However, when the four bacterial strains of GN02, *Ottowia, Sneathia*, and *Lautropia* were adopted as the detection target, the test subject group who had contracted periodontal disease had a sum total of the number of sequence reads thereof that did not exceed 0.01% of the sum total of the number of sequence reads detected.

It is apparent from the above results that the periodontal disease diagnostic method including the process to detect in the specimen at least one bacterial strain selected from the

TABLE 2

| | Test Subject | | | | | | | | |
|---|---|---|---|---|---|---|---|---|---|
| | C1 | C2 | C3 | C4 | C5 | C6 | C7 | C8 | C9 |
| GN02 | 0.1539 | 0.0286 | 0.0000 | 0.0514 | 0.0304 | 0.0000 | 0.3217 | 0.1058 | 0.0703 |
| Ottowia | 0.0118 | 0.0143 | 0.0273 | 0.0835 | 0.0819 | 0.0000 | 0.1488 | 0.0735 | 0.0091 |
| Sneathia | 0.0118 | 0.0143 | 0.0000 | 0.0000 | 0.0000 | 0.0142 | 0.0000 | 0.0064 | 0.0476 |
| Lautropia | 0.1775 | 0.0571 | 0.0273 | 0.1349 | 0.1123 | 0.0142 | 0.4705 | 0.1858 | 0.1270 |
| O + S | 0.0237 | 0.0286 | 0.0273 | 0.0835 | 0.0819 | 0.0142 | 0.1488 | 0.0800 | 0.0567 |
| L + S | 0.1894 | 0.0714 | 0.0273 | 0.1349 | 0.1123 | 0.0283 | 0.4705 | 0.1922 | 0.1746 |
| All | 0.3551 | 0.1143 | 0.0547 | 0.2699 | 0.2246 | 0.0283 | 0.9411 | 0.3715 | 0.2540 |

| | Test Subject | | | | | | | |
|---|---|---|---|---|---|---|---|---|
| | D1 | D2 | D3 | D4 | D5 | D6 | D7 | D8 |
| GN02 | 0.0000 | 0.0000 | 0.0000 | 0.0000 | 0.0000 | 0.0000 | 0.0000 | 0.0000 |
| Ottowia | 0.0000 | 0.0000 | 0.0000 | 0.0000 | 0.0000 | 0.0000 | 0.0000 | 0.0000 |
| Sneathia | 0.0000 | 0.0000 | 0.0000 | 0.0000 | 0.0000 | 0.0000 | 0.0000 | 0.0000 |
| Lautropia | 0.0000 | 0.0000 | 0.0000 | 0.0000 | 0.0000 | 0.0000 | 0.0000 | 0.0000 |
| O + S | 0.0000 | 0.0000 | 0.0000 | 0.0000 | 0.0000 | 0.0000 | 0.0000 | 0.0000 |
| L + S | 0.0000 | 0.0000 | 0.0000 | 0.0000 | 0.0000 | 0.0000 | 0.0000 | 0.0000 |
| All | 0.0000 | 0.0000 | 0.0000 | 0.0000 | 0.0000 | 0.0000 | 0.0000 | 0.0000 |

Detection Result Review

When GN02, *Ottowia, Sneathia*, or *Lautropia* was individually adopted as the detection target, the test subject group who had not contracted periodontal disease had a sum total of the number of sequence reads of the at least one bacterial strain exceeding 0.01% of the sum total of the number of sequence reads detected. Within these results, for all of the test subjects the number of sequence reads of *Lautropia* exceeded 0.01% of the sum total of the number of sequence reads detected. However, when GN02, *Ottowia, Sneathia*, or *Lautropia* was individually adopted as the detection target, the test subject group who had contracted periodontal disease had a number of sequence reads thereof that in each case did not exceed 0.01% of the sum total of the number of sequence reads detected.

In cases in which two bacterial strains of *Ottowia* and *Sneathia*, or when two bacterial strains of *Lautropia* and *Sneathia*, were adopted as the detection target, the test group consisting of GN02, *Ottowia, Sneathia*, and *Lautropia* is useful in the evaluation of the possibility that the specimen provider has contracted periodontal disease.

The entire contents of the disclosure of Japanese Patent Application Nos. 2017-038122 and 2017-038123 are incorporated by reference in the present specification.

All publications, patent applications and technical standards mentioned in the present specification are incorporated by reference in the present specification to the same extent as if each individual publication, patent application, or technical standard was specifically and individually indicated to be incorporated by reference.

SEQUENCE LISTING

International Patent Application MT-F03217-JP18007622_2.app under the International Patent Cooperation Treaty.

The invention claimed is:

1. A periodontal disease detection method comprising: (i) a detection process to detect in a specimen at least two bacterial strains selected from the group consisting of *Anaeroglobus, Cryptobacterium, Desulfobulbus, Desulfomicrobium, Desulfovibrio*, Erysipelotrichaceae, Fretibacterium, *Johnsonella, Mitsuokella*, Mollicutes, *Parascardovia, Pseudoramibacter, Pyramidobacter, Scardovia, Shuttleworthia*, and *Mycoplasma*, and (ii) an evaluation process after the detection process to evaluate a possibility that a specimen provider has contracted periodontal disease as high in cases in which a sum total of a number of sequence reads of the at least two bacterial strains included in the group is 0.02% or more with respect to a sum total of a number of sequence reads obtained in the detection process of 100%.

2. The periodontal disease detection method of claim 1, wherein the at least two bacterial strains included in the group are at least two bacterial strains selected from the group consisting of *Anaeroglobus*, Fretibacterium, and *Mycoplasma*.

3. The periodontal disease detection method of claim 1, wherein the detection is performed by metagenomic analysis.

4. The periodontal disease detection method of claim 1, wherein the specimen is saliva.

5. A periodontal disease detection system comprising: (i) a detection section to detect in a specimen at least two bacterial strains selected from the group consisting of *Anaeroglobus, Cryptobacterium, Desulfobulbus, Desulfomicrobium, Desulfovibrio*, Erysipelotrichaceae, Fretibacterium, *Johnsonella, Mitsuokella*, Mollicutes, *Parascardovia, Pseudoramibacter, Pyramidobacter, Scardovia, Shuttleworthia*, and *Mycoplasma*, and (ii) an evaluation section to evaluate a possibility that a specimen provider has contracted periodontal disease as high in cases in which a sum total of a number of sequence reads of the at least two bacterial strains included in the group is 0.02% or more with respect to a sum total of a number of sequence reads obtained by the detection section of 100%.

6. A periodontal disease detection kit comprising: (i) a detection device to detect in a specimen at least two bacterial strains selected from the group consisting of *Anaeroglobus, Cryptobacterium, Desulfobulbus, Desulfomicrobium, Desulfovibrio*, Erysipelotrichaceae, Fretibacterium, *Johnsonella, Mitsuokella*, Mollicutes, *Parascardovia, Pseudoramibacter, Pyramidobacter, Scardovia, Shuttleworthia*, and *Mycoplasma*, and (ii) an evaluation device to evaluate a possibility that a specimen provider has contracted periodontal disease as high in cases in which a sum total of a number of sequence reads of the at least two bacterial strains included in the group is 0.02% or more with respect to a sum total of a number of sequence reads obtained by the detection section of 100%.

7. A periodontal disease detection method including: (i) a detection process to detect in a specimen at least one bacterial strain selected from the group consisting of GN02, *Ottowia, Sneathia*, and *Lautropia*, and (ii) an evaluation process after the detection process to evaluate a possibility that a specimen provider has contracted periodontal disease as high in cases in which a sum total of a number of sequence reads of the at least one bacterial strain included in the group is 0.01% or less with respect to a sum total of a number of sequence reads obtained in the detection process of 100%.

8. The periodontal disease detection method of claim 7, wherein the detection is performed by metagenomic analysis.

9. The periodontal disease detection method of claim 7, wherein the specimen is saliva.

10. The periodontal disease detection method of claim 7, wherein the at least one bacterial strain included in the group includes *Lautropia*.

11. The periodontal disease detection method of claim 7, wherein the at least one bacterial strain included in the group is a combination of *Lautropia* combined with at least one bacterial strain selected from the group consisting of GN02, *Ottowia*, and *Sneathia*.

12. A periodontal disease detection system comprising: (i) a detection section to detect in a specimen at least one bacterial strain selected from the group consisting of GN02, *Ottowia, Sneathia*, and *Lautropia*, and (ii) an evaluation section to evaluate a possibility that a specimen provider has contracted periodontal disease as high in cases in which a sum total of a number of sequence reads of the at least two bacterial strains included in the group is 0.01% or more with respect to a sum total of a number of sequence reads obtained by the detection section of 100%.

13. A periodontal disease detection kit comprising: (i) a detection device to detect in a specimen at least one bacterial strain selected from the group consisting of GN02, *Ottowia, Sneathia*, and *Lautropia*, and (ii) an evaluation device to evaluate a possibility that a specimen provider has contracted periodontal disease as high in cases in which a sum total of a number of sequence reads of the at least two bacterial strains included in the group is 0.01% or more with respect to a sum total of a number of sequence reads obtained by the detection section of 100%.

* * * * *

SEQUENCE LISTING

```
<160> NUMBER OF SEQ ID NOS: 4

<210> SEQ ID NO 1
<211> LENGTH: 17
<212> TYPE: DNA
<213> ORGANISM: Artificial Sequence
<220> FEATURE:
<223> OTHER INFORMATION: F primer for V3-V4
<220> FEATURE:
<221> NAME/KEY: misc_feature
<222> LOCATION: (9)..(9)
<223> OTHER INFORMATION: n is a, c, g, or t

<400> SEQUENCE: 1
cctacgggng gcwgcag                                                        17

<210> SEQ ID NO 2
<211> LENGTH: 21
<212> TYPE: DNA
<213> ORGANISM: Artificial Sequence
<220> FEATURE:
<223> OTHER INFORMATION: R primer for V3-V4

<400> SEQUENCE: 2
gactachvgg gtatctaatc c                                                   21

<210> SEQ ID NO 3
<211> LENGTH: 19
<212> TYPE: DNA
<213> ORGANISM: Artificial Sequence
<220> FEATURE:
<223> OTHER INFORMATION: F primer for V4

<400> SEQUENCE: 3
gtgccagcmg ccgcggtaa                                                      19

<210> SEQ ID NO 4
<211> LENGTH: 20
<212> TYPE: DNA
<213> ORGANISM: Artificial Sequence
<220> FEATURE:
<223> OTHER INFORMATION: R primer for V4

<400> SEQUENCE: 4
ggactachvg ggtwtctaat                                                     20
```